United States Patent
Heinen et al.

(10) Patent No.: US 10,215,826 B2
(45) Date of Patent: Feb. 26, 2019

(54) MPI SCANNER WITH MOVING PERMANENT MAGNETIC ELEMENTS

(71) Applicant: Bruker BioSpin MRI GmbH, Ettlingen (DE)

(72) Inventors: Ulrich Heinen, Ettlingen (DE); Jochen Franke, Karlsruhe (DE)

(73) Assignee: Bruker BioSpin MRI GmbH, Ettlingen (DE)

( * ) Notice: Subject to any disclaimer, the term of this patent is extended or adjusted under 35 U.S.C. 154(b) by 296 days.

(21) Appl. No.: 15/000,137

(22) Filed: Jan. 19, 2016

(65) Prior Publication Data

US 2016/0216353 A1 Jul. 28, 2016

(30) Foreign Application Priority Data

Jan. 22, 2015 (EP) .................................... 15152127

(51) Int. Cl.
*G01R 33/56* (2006.01)
*G01R 33/02* (2006.01)
(Continued)

(52) U.S. Cl.
CPC ........ *G01R 33/5601* (2013.01); *A61B 5/0035* (2013.01); *A61B 5/055* (2013.01);
(Continued)

(58) Field of Classification Search
CPC G01R 33/5601; G01R 33/0213; G01R 33/10; G01R 33/1276; G01R 33/383;
(Continued)

(56) References Cited

U.S. PATENT DOCUMENTS 9,927,500 B2 3/2018 Heidenreich
2002/0097199 A1* 7/2002 Matsuura ................ G02F 1/167
345/30
(Continued)

OTHER PUBLICATIONS

Patrick Vogel et al., "Traveling Wave Magnetic . . . ," IEEE Transactions on Medical Imaging, vol. 33, No. 2, Feb. 2014.
(Continued)

*Primary Examiner* — Gregory H Curran
(74) *Attorney, Agent, or Firm* — Paul Vincent

(57) ABSTRACT

An MPI-apparatus comprising a magnet system for generating a time-varying and position-dependent magnetic field and a detection system detecting signals from MPI contrast agents exposed to said magnetic field within a detection volume, said signals being suitable for reconstructing an image of the spatial and temporal distribution of said MPI contrast agents, is characterized in that the magnet system comprises an array with a plurality of permanent magnetic elements geometrically arranged in such a way that at least a part of the plurality of permanent magnetic elements are moved with sufficient speed in the vicinity of the detection volume to create the spatial and temporal magnetic field variations for inducing within the contrast agent the MPI signals recorded by the detection system. This avoids the high power requirements of current MPI scanners, while opening the way for higher spatial resolutions and variable scanning frequencies.

15 Claims, 8 Drawing Sheets

(51) Int. Cl.

| | | |
|---|---|---|
| *G01R 33/10* | (2006.01) | |
| *G01R 33/12* | (2006.01) | |
| *A61B 5/00* | (2006.01) | |
| *A61B 5/055* | (2006.01) | |
| *G01R 33/383* | (2006.01) | |
| *G01R 33/48* | (2006.01) | |
| *A61B 5/05* | (2006.01) | |

(52) U.S. Cl.
CPC ......... *G01R 33/0213* (2013.01); *G01R 33/10* (2013.01); *G01R 33/1276* (2013.01); *G01R 33/383* (2013.01); *G01R 33/4808* (2013.01); *A61B 5/0515* (2013.01)

(58) Field of Classification Search
CPC ... G01R 33/4808; A61B 5/0515; A61B 5/055; A61B 5/0035
See application file for complete search history.

(56) References Cited

U.S. PATENT DOCUMENTS

2011/0221438 A1* 9/2011 Goodwill ............... G01R 33/10
324/301
2015/0008910 A1 1/2015 Goodwill

OTHER PUBLICATIONS

Yumi Ijiri et al., "Inverted Linear Halbach . . . ," IEEE Transactions on Magnetics, vol. 49, No. 7, Jul. 2013.
Patrick W. Goodwill et al., "Projection X-SPace . . . ", IEEE Transactions on Medical Imaging, vol. 31, No. 5, May 2012.
Bernhard Gleich et al., "Tomographic imaging using . . . ," Nature, vol. 435/30, Jun. 2005.
J. Weizenecker et al., "Three-dimensional real-time . . . ," Phys. Med. Biol. 54 (2009) L1-L10.
Patrick W. Goodwill et al., "An x-Space magnetic particle . . . ," Review of Scientific Instruments 83, 033708 (2012).
Juergen Weizenecker et al., "Magnetic particle imaging . . . ," J. Phys. D:Appl. Phys. 41 (2008) 105009.
Tobias Knopp et al., "Efficient generation . . . ," Med. Phys. 37 (7), Jul. 2010.
Marlitt Erbe et al., "Experimental generation . . . ," Med. Phys. 38(9), Sep. 2011.
P. Klauer et al., "Magnetic Particle imaging . . . ," Proc. Intl. Soc. Mag. Reson. Med. 19 (2011).
Patrick Vogel et al., "Ultra High Resolution . . . ," International Workshop on Magnetic Particle Imaging, 2014.
A. Timmermeyer et al., "Super-resolution approaches . . . ," International Workshop on Magnetic Particle Imaging (VMPI) 2013, Abstract 43.

* cited by examiner

Fig. 2

MPI SCANNER WITH MOVING PERMANENT MAGNETIC ELEMENTS

The invention relates to an MPI-(=Magnetic Particle Imaging) apparatus comprising a magnet system designed for the generation of a time-varying and position-dependent magnetic field in a detection volume and a detection system detecting signals from MPI contrast agents exposed to said magnetic field within said detection volume, said signals being suitable for reconstructing an image of the spatial— and where required also temporal—distribution of said MPI contrast agents.

BACKGROUND OF THE INVENTION

Such apparatus is known from a publication of P. Klauer, M. A. Rückert, P. Vogel, W. H. Kullmann, P. M. Jakob, V. C. Behr, *Proc. Intl. Soc. Mag. Res. Med.* 2011, 19, 3783 (see Reference [8] below).

Brief Introduction to MPI

Magnetic Particle Imaging (MPI) is a new ultra-fast tracer-based imaging technology with promising applications particularly in cardio-vascular research and diagnosis.

In MPI, contrast agent such as Super-Paramagnetic Iron Oxide Nano-Particles (SPIOs) are exposed to a magnetic field (Drive Field) that oscillates in 1-3 spatial dimensions. The non-linear magnetization change of these particles generates an electromagnetic signal which contains contributions at higher harmonics of the excitation signal. This signal can be detected by suitable detection coils and an image can be reconstructed. A strong gradient field (Selection Field, SF) saturates the particle magnetization everywhere except for a small Field Free Region (=FFR), thereby confining the signal generation to this region. The Drive Field shifts this FFR in space, and the passage of the FFR over the Super-Paramagnetic Iron Oxide Nano-Particles induces the aforementioned non-linear magnetization change. The topology of the Field Free Region can be either a point (Field Free Point, FFP scanners) or a line (Field Free Line, FFL scanners) depending on the layout of the Selection Field. The advantage of FFL scanners is that they obtain signal from a larger volume at each instant of time, thereby achieving a higher SNR. As the signal at a given point of time comes from particles in multiple positions along the FFL, the encoding scheme must sample each object position with different FFL orientations to allow unambiguous image reconstruction.

PREVIOUS WORK

The first MPI implementations were using two permanent magnets to generate the selection field, and a single channel Helmholtz coil pair in a resonant circuit for signal excitation and scanning along one direction (drive field). Two more imaging dimensions were realized by mechanical movement of the sample orthogonal to the drive field direction (see Reference [1]).

To avoid the slow mechanical movement of the sample, the first successful 3D scanner used three orthogonal drive field coil pairs operating at slightly different frequencies, thereby sampling the field of view along a Lissajous trajectory. The field free point was again realized by strong permanent magnets (see Reference [2])

This design was later extended by adding additional Helmholtz-like coil pairs (Focus field coils) along the principal directions for shifting the Field of View (=FOV) over a larger distance.

This design is currently being commercialized by Bruker with the important modification of replacing the permanent magnets that create the selection field by a resistive design.

Based on the same general layout a scanner was demonstrated (see Reference [3]) with a single drive field channel and two focus field channels. In this scanner, the FFP oscillates along a line parallel to the scanner bore, and this line is slowly shifted by the focus field coils. Images are obtained via a different reconstruction technique termed X-Space. In this concept, the local particle concentration is in principle obtained directly by plotting the signal intensity as a function of the FFP position after correction for the position-dependent FFP speed.

Designs for an FFL scanner were proposed and later refined (see References [4], [5], [6]) in which a Field Free Line is generated by a set of resistive coil pairs across the scanner bore where the FFL rotates in space around the scanner axis while being shifted laterally along the scanner axis and perpendicular to it at two different frequencies. Initial results of this scanner design are promising.

An alternative scanner design has been demonstrated (see Reference [7]) which provides a straight FFL with a gradient strength of dB/dz=2.35 T/m along a gap by placing strong permanent magnets on either side with identical poles facing each other. The scanner bore is perpendicular to this field gap, and resistive magnets are installed that can shift the FFL along the bore or perpendicular to it, whereby the movement along the bore provides the high-frequency excitation signal. Reconstruction is achieved via filtered back-projection and requires rotation of the imaged object around the scanner axis.

Yet a different design termed Travelling Wave MPI (TWMPI) has been shown where the sinusoidal excitation is generated by a solenoid coil around the scanner bore split into multiple sections which are then driven with a phase offset. This design allows a large scale FFP movement with constant speed along one direction without the necessity of very high excitation amplitudes (see Reference [8]). Essentially, the Travelling Wave MPI scanner produces the saturation field and the drive field by the same set of coils, where the maximum gradient direction is along the path of the FFP. The reconstruction is similar to the X-space reconstruction but requires no speed correction.

Recent work of the same group demonstrates the use of permanent magnet rings to generate an ultra-high field gradient and generation of a line profile of a Super-Paramagnetic Iron Oxide Nano-Particles sample moved along the axis of this ring arrangement (see Reference [9]).

Problems of Current MPI Scanners

Power Demands

The design of current MPI scanners with resistive coils is characterized by high power and cooling demands, very high demands on component linearity and spectral purity, while inherent limits for the Field of View and the Temporal and Spatial resolution exist, which can only be overcome by further increasing the power and cooling demands.

Interdependency of Temporal Resolution, Spatial Resolution, and Field of View

The achievable spatial resolution depends on the properties of the employed tracers and the steepness of the field gradient of the Selection Field around the FFR. Practical implementations have used gradient strengths in the range of 1 T/m to 12 T/m. To achieve a certain Field of View, the Drive Field must be sufficiently strong to move the FFR over the required distance. Hence, a stronger Selection Field also requires a stronger Drive Field. The necessary Drive Field amplitudes may be difficult to achieve for a larger Field of View. Current solutions are to either reduce the Selection Field gradient strength (at the expense of spatial resolution) or to implement a large-scale low-speed shift of the FFR by an additional set of so-called Focus Field (FF) coils at the expense of temporal resolution.

Fixed Frequency

The imaging performance of MPI contrast agent such as Super-Paramagnetic Iron Oxide Nano-Particles tracer materials critically depends on the chosen excitation frequencies as the magnetization change will not occur instantaneously. Instead, two different mechanisms (Néel relaxation and Brownian Rotation) with different time constants contribute to the magnetization change. For tracer-materials with a larger distribution of particle sizes and shapes, both mechanisms must be characterized by a distribution of relaxation times, and in practice it is difficult to predict the optimum excitation frequency which will lead to the best SNR performance of an MPI scanner. Excluding all instrumental factors and PNS/SAR issues, the excitation frequency $\omega_{DF}$ should be as high as possible but obey the condition $\omega_{DF} \ll \tau_{relax}$, where $\tau_{relax}$ is the effective relaxation time of the tracer material.

Unfortunately, most current scanner designs operate the Drive Field system in resonant loops to achieve the required field strengths, and the excitation frequency cannot easily be changed.

Filtering Problems

A problem of current MPI scanners is that the Drive Field induces a signal in the detection coils which is several orders of magnitude stronger than the particle response. To damp the excitation signal, gradiometer arrangements for the detection coils have been employed, but perfect cancellation is typically difficult to achieve due to geometric constraints. A different approach uses spectral filtering by ensuring a very clean sinusoidal excitation signal which is then suppressed in the detection signal, thereby singling out the higher harmonics of the excitation signal which are created by the Super-Paramagnetic Iron Oxide Nano-Particles. The latter method restricts the scanner operation to a single excitation frequency.

Both approaches are often combined. Construction of hardware for pure sinusoidal excitation at high power levels is very demanding. Likewise, the requirements for the band stop filters in the receive path are high. The loss of the fundamental in the acquired signal poses problems for the image reconstruction.

SUMMARY OF THE INVENTION

Object of the Invention

It is therefore an object of the invention to provide a generic MPI-apparatus with the features defined in the preamble part of claim 1, which allows to avoid the high power requirements of current MPI scanners, while opening the way for higher spatial resolutions and variable scanning frequencies.

Short Description of the Invention

This object is achieved, in accordance with the invention, by an MPI apparatus method as introduced in the beginning and defined in the preamble part of claim 1, characterized in that the magnet system comprises an array with a plurality of permanent magnetic elements geometrically arranged in such a way that at least a part of the plurality of permanent magnetic elements are moved with sufficient speed in the vicinity of the detection volume to create the spatial and temporal magnetic field variations for inducing within the contrast agent the MPI signals recorded by the detection system.

The setup of an MPI system with permanent magnets is cost effective and does not require the use of high electric currents to generate varying magnetic fields.

Preferred Variants of the Invention

In a preferred embodiment of the MPI apparatus according to the present invention, the magnetic elements are arranged in neighboring pairs whereby the magnetic elements of each pair have opposite polarity, respectively. Thereby a Field Free Region (FFR) can be generated in a simple manner.

A class of further embodiments of the present invention is characterized in that the magnetic elements are geometrically arranged on one or more transport or conveyor belts in the form of closed loops. This has the advantage that the magnets can be guided on a flexible trace. A linear part of the transport of conveyor belt further allows an easy extension of the spatial measuring range. Several detection systems may be used to allow multi-sample investigation.

Alternatively—or maybe even in combination thereto—in preferred embodiments, the MPI-apparatus according to the invention can be characterized in that the magnetic elements are geometrically arranged in the form of one or more wheels, in particular with the magnetic elements being positioned in a plane defined by the wheel. Thereby high speed periodic variations of the magnetic field for short term investigation of the samples can be achieved.

In a class of further developments, these embodiments can be modified in that the wheels are geometrically arranged in a coaxial manner relative to each other. Thereby the MPI apparatus requires less space, and multiple detection setups are possible.

Alternatively—or maybe even in combination thereto—in other modifications at least some of the wheels are geometrically arranged in a non-coaxial manner relative to one another. This has the advantage that the detection volume has a good accessibility and the magnetic forces between the wheels is minimum.

The above embodiments of the MPI-apparatus according to the invention can also be modified in that the closed loops or wheels are movable at variable speed. This allows investigations with different temporal resolutions and especially an adaption of the investigation to the relaxation properties of the MPI contrast agent.

In these modifications, it can be of special advantage if the closed loops or wheels are movable, in particular rotatable at different speeds. Thereby, different temporal magnetic field sequences in the detection volume can be realized.

A further group of modifications is characterized in that the detection system comprises detection coils arranged at positions of equivalent magnetic field change between neighboring permanent magnetic elements, especially at opposite positions of the wheels. Thereby the induction of current into the detection coils by the permanent magnet elements can be minimized resulting in a higher sensitivity for an MPI signal. This may be achieved by suitable cross-connection of related detection coils.

It is generally preferable, when the pairs of magnetic elements—as discussed above—are arranged radially within a closed loop or wheel. This allows a good access to the detection volume.

These modification can be advantageously further developed in that each pair of magnetic elements is complemented by another pair of magnetic elements being positioned on an opposite side of the wheel with respect to the axis of the wheel and that each of complementary pairs is positioned at identical radial displacement with respect to said axis. Thereby the imbalance of the wheel is minimized.

In a further class of embodiments, the MPI-apparatus according to the present invention may be characterized in that the magnetic elements are arranged in a way such as to provide spatial encoding of the magnetic particles within the MPI sample being measured. By this means a defined sampling of the detection volume becomes possible.

In an alternative class of embodiments, the MPI-apparatus can be characterized in that the magnetic elements are arranged in a way such as to produce a sinusoidal varying magnetic field at the sample position. This allows generation of a variable frequency magnetic field for spectroscopic applications, e.g. for characterisation of MPI contrast agents.

Further embodiments of the MPI-apparatus according to the present invention are characterized in that the magnetic elements are arranged in way to allow for driving the MPI-apparatus in a FFL (=field free line) or in a FFP (=field free point) mode. By use of a FFL mode a higher sensitivity can be achieved whereas an FFP mode allows a simple setup of the investigation.

In another embodiment the MPI-apparatus further comprising auxiliary coils D for generating an offset field to shift the magnetic field in the detection volume. Thereby a subcoding below the resolution given by the positions of the mechanically fixed magnets can be achieved.

Last, but not least, an MPI-apparatus according to the present invention may be of advantage, in which at least one magnetic element pair is arranged in way to generate homogenous magnetic field sections suitable for MRI (=magnetic resonance imaging), i.e. the magnetic element pairs facing each other with complementary poles. Magnetic resonance imaging is a powerful, non-invasive tool for obtaining spatially resolved information of objects, in particular parts of a body of a living human or animal.

Further advantages can be extracted from the description and the enclosed drawing. The features mentioned above and below can be used in accordance with the invention either individually or collectively in any combination. The embodiments mentioned are not to be understood as exhaustive enumeration but rather have exemplary character for the description of the invention.

DRAWING

Embodiments of the invention are depicted in detail in the figures of the drawing:

Note inversion symmetry between both field free regions, implying that identical signals are generated in the coil sets B and C with the exception of the top/bottom coils, which exhibit an inverted signal.

The figure intends to illustrate the principle and is not drawn to scale for an actual implementation of the scanner.

Figure 2:
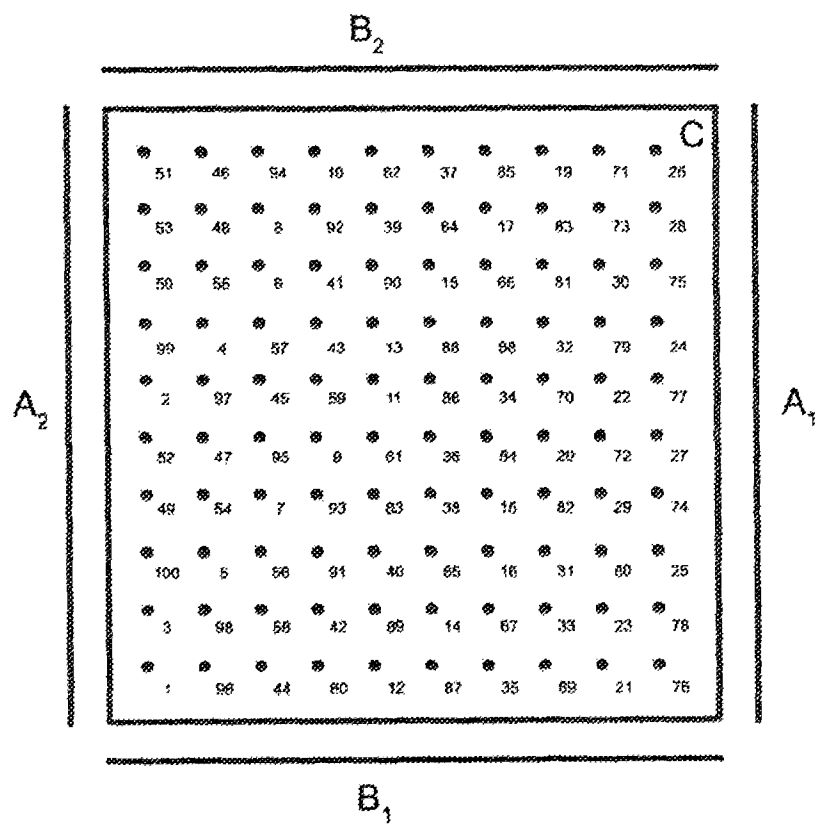

FIG. 2 shows detail of imaging plane between detection coil set. A possible encoding scheme for 100 distinct magnet pairs (FFP positions) is shown that fulfils the criteria of no static imbalance and negligible dynamic imbalance. Rotation axis is to the right. A1/A2: Inner/Outer coil pair, B1/B2: Top/Bottom coil pair, C: Tangential coil.

Figure 3:
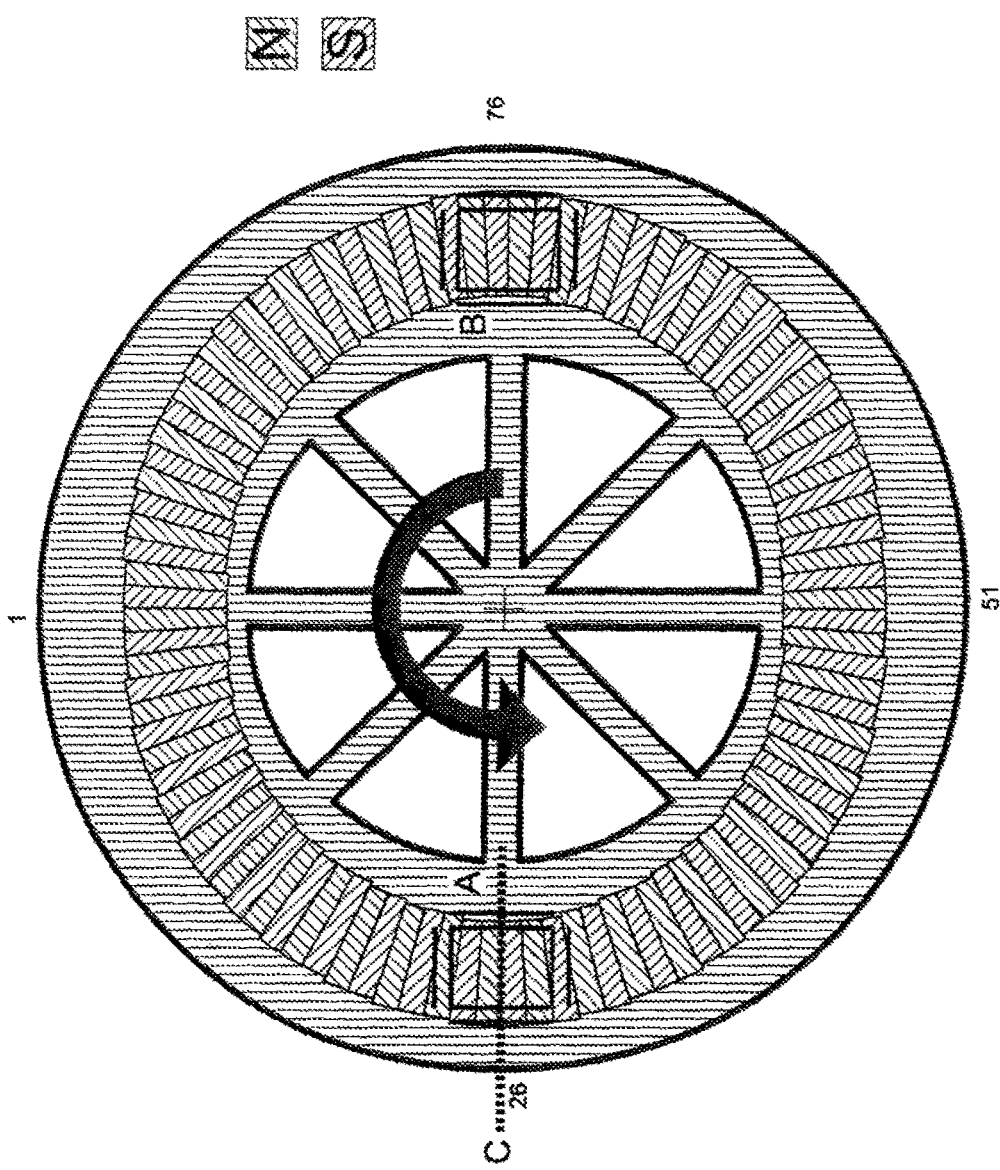

FIG. 3 shows a radial magnet arrangement within one wheel for scanner with 100 distinct FFP positions implementing the encoding scheme shown in FIG. 2 by placing magnets at different radial positions while maintaining twofold symmetry for balancing purposes. A: Detection coil set, B: Compensation coil set. C: one example imaging plane that would show the FFP traversals as in FIG. 2.

Note that for an FFP scanner it is not strictly necessary that neighbouring magnet pairs are mounted without gaps. A simple setup with circular, rod like, or square magnets is sufficient to generate the sequence of FFPs.

The figure intends to illustrate the principle and is not drawn to scale for an actual implementation of the scanner.

Figure 4:
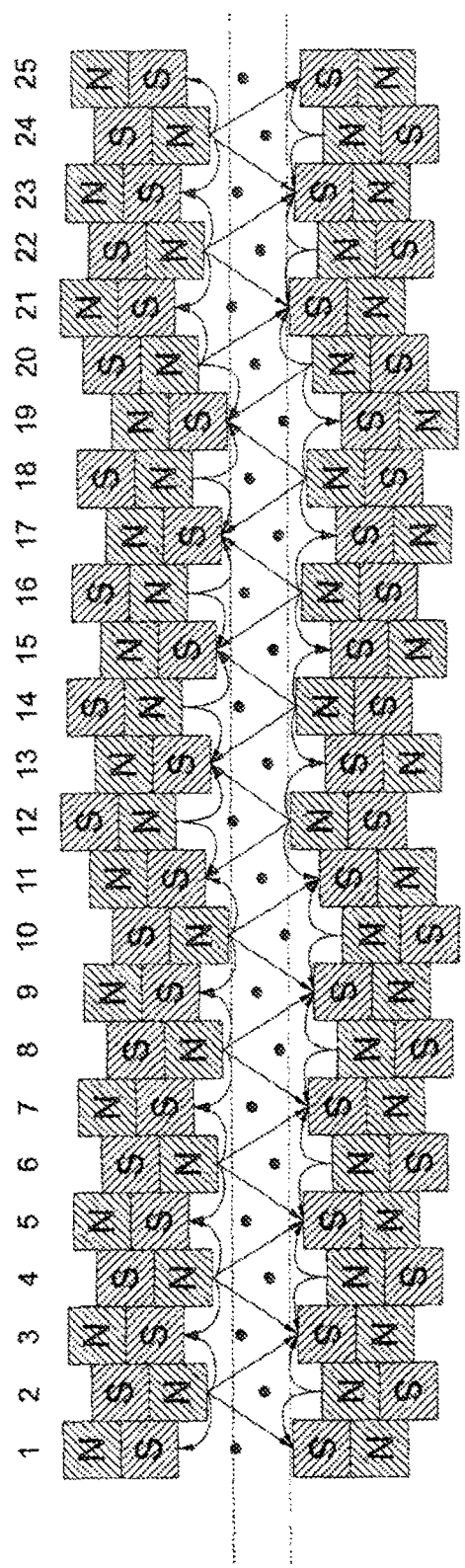

FIG. 4 shows an arrangement of magnet pairs in the perimeter of the rotating magnet layout. The image shows the top-left quarter of the magnet arrangement shown in FIG. 3 for generating the encoding scheme of FIG. 2. A few field lines and the positions of the FFPs (black dots) are shown. The height of the possible imaging volume is indicated by dotted lines.

The figure intends to illustrate the principle and is not drawn to scale for an actual implementation of the scanner.

Figure 5:
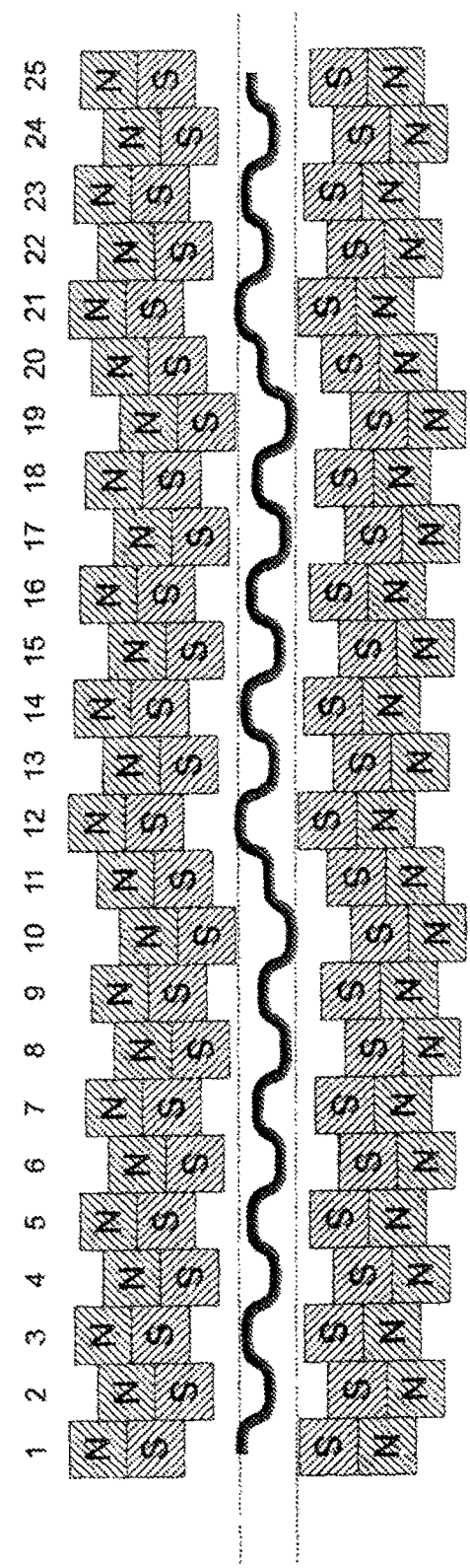

FIG. 5 shows the same wheel perimeter section as in FIG. 4, but without polarity alternation of the magnet pairs. The field free points coalesce into a field free line. In this setup it is essential that neighbouring magnets are mounted without gaps, otherwise the field lines can "escape" between the magnets and a field free line is no longer created.

Figure 6:
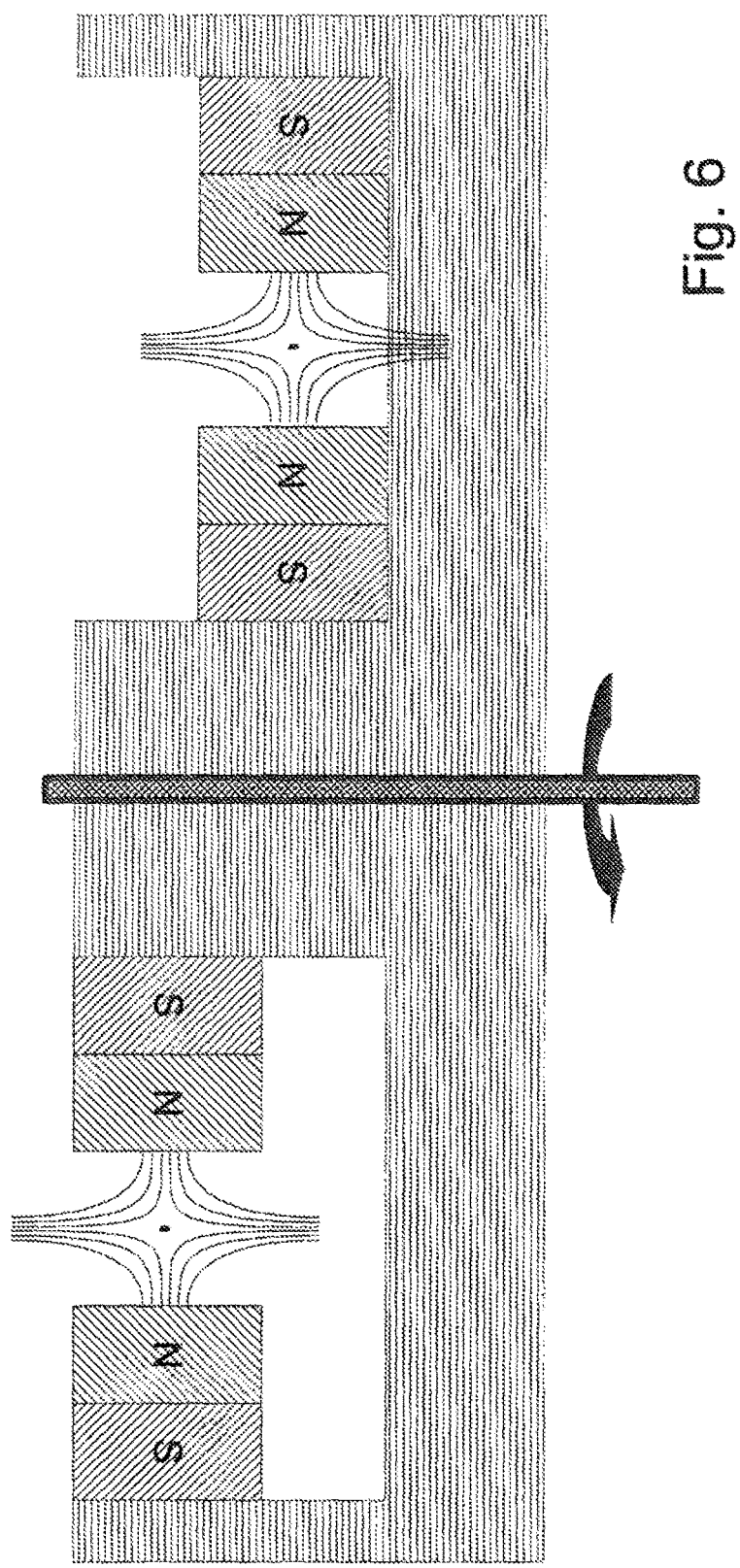

FIG. 6 shows a cross section of an alternative design where the magnet pairs are aligned radially rather than parallel to the axis of rotation, generating a groove in which the FFPs/the FFL is located.

Figure 7:
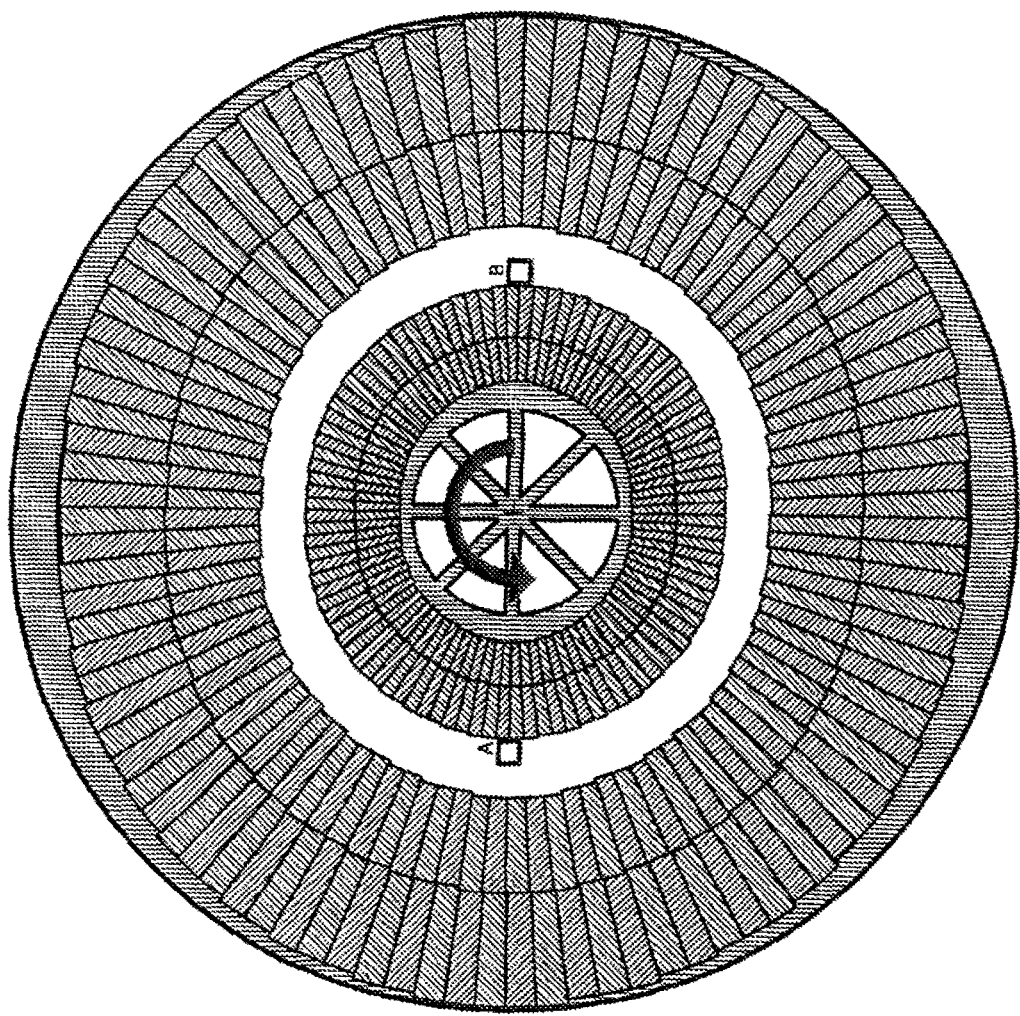

FIG. 7 shows an axial view of the alternative magnet layout shown in FIG. 6. A: site for detection coil set and imaging volume, B: site for compensation coil set.

Figure 8:
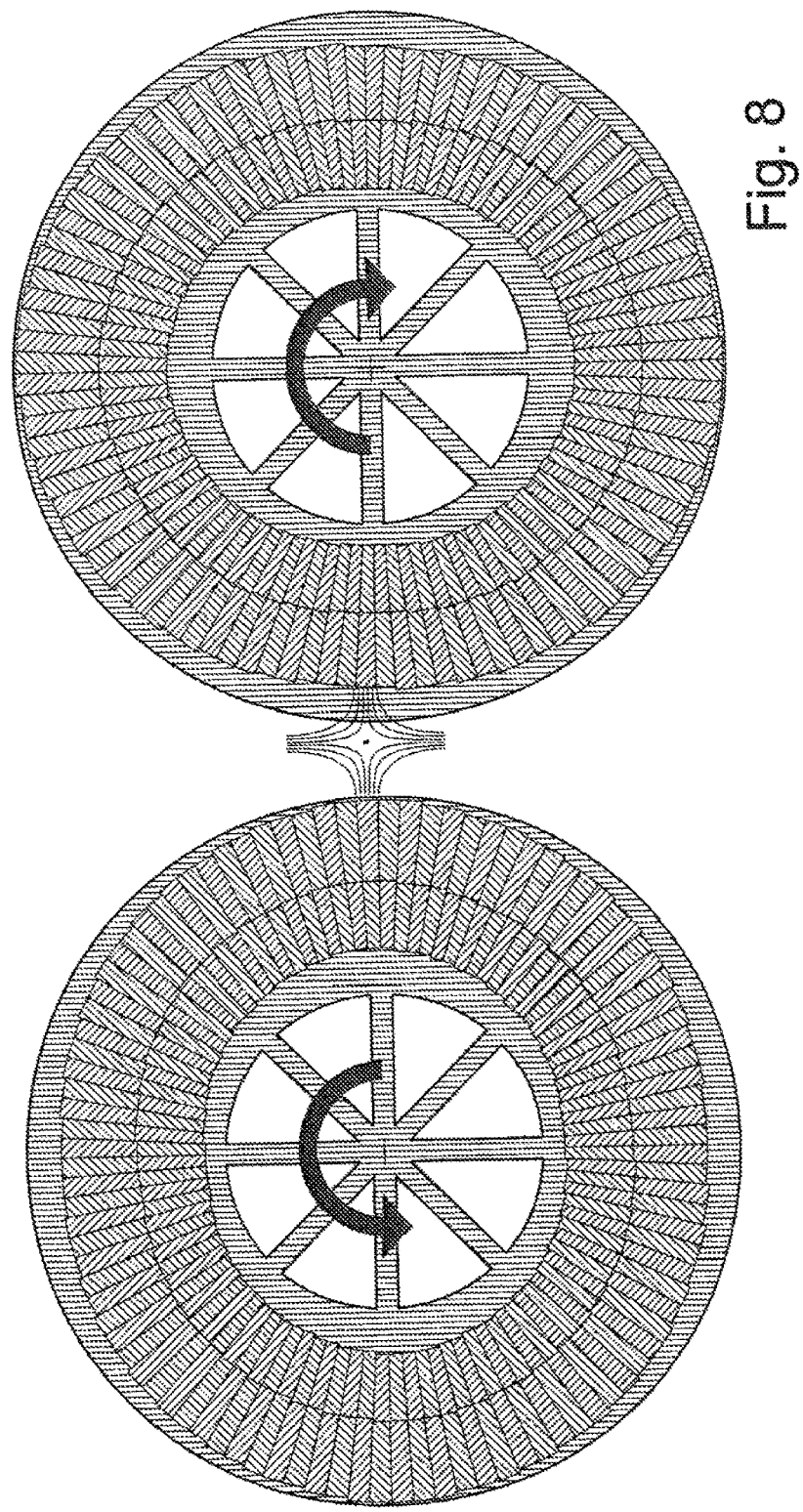

FIG. 8 shows an alternative scheme with radially oriented magnets arranged on two wheels, rotating in opposite direction with the same speed. The shown configuration generates a sequence of 100 FFPs in the imaging volume between the wheels. Note that in this setup one can alternatively generate a sequence of alternative homogenous fields simply by advancing one axis by 3.6° with respect to the other.

DESCRIPTION OF PREFERRED EMBODIMENTS

In the following, the invention is discussed in detail by way of examples:

Proposed New Scanner Design

1. Basic Design Idea

Conventional FFP or FFL scanners generate the FFR by one set of electromagnets or permanent magnets (selection field) and then use another set of electromagnets (drive field) to move it in space. In some cases, additional slow sample movement is required to achieve full 3D encoding.

Rotating Wheel Scanner

The present proposal eliminates the drive field coils by moving the selection field magnet assembly instead. This will create a movement of the FFR relative to the imaged object. As the magnet assembly will typically have high moments of inertia, an oscillating motion would be impeded by the required large forces. Therefore, the proposed design arranges the FFR creating magnets on the perimeter of two wheels mounted on a common axis with a certain gap size.

Magnet Arrangement for FFP Scanning

Figure 1:
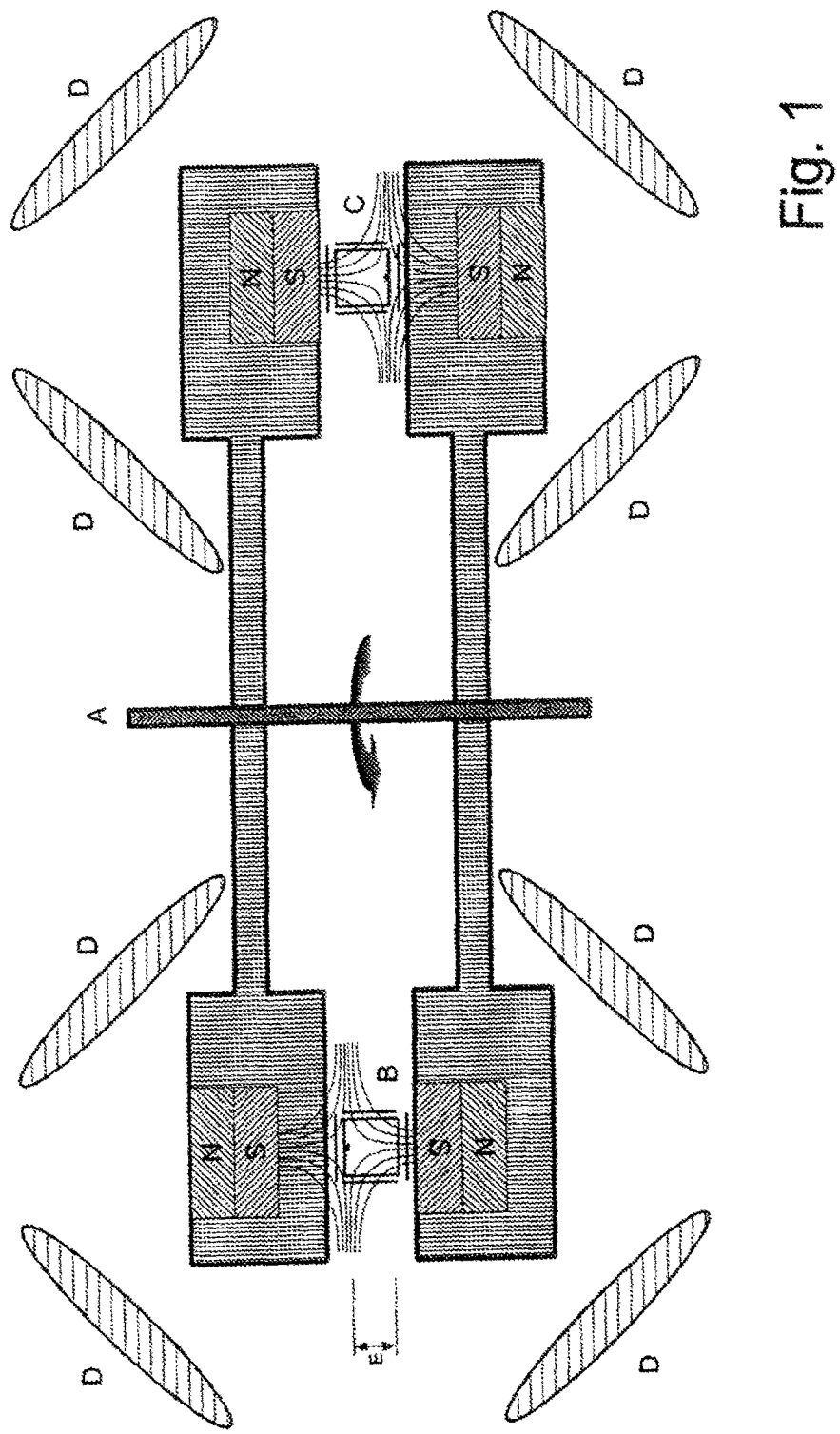
FIG. 1 shows a cross section through the proposed scanner. The gradient generating magnet pairs are held by two opposing rotating wheels mounted on a common rotation axis. Each magnet pair generates a field free region at half distance between the poles (black dots). A: Rotation axis, B: Detection coil set, C: compensation coil set, D: Small range shift coils for super resolution imaging (subencoding), E: Field of View height, F wheel construction, G permanent magnets.

If neighboring magnet pairs are arranged to have opposite polarity, a sequence of FFPs arranged in a circle is generated (see FIG. 4). Movement of an FFP through a sample placed at any angular position between the rotating wheels will generate an electromagnetic signal whose time profile corresponds to the Super-Paramagnetic Iron Oxide Nano-Particles concentration profile along the FFP path (first encoding direction). By placing each magnet pair at different radial and lateral positions, each FFP will travel along a unique circular path during rotation. The magnet positions can be chosen in a way that the intersections of the FFP paths with a plane that includes the rotation axis (Imaging Plane, IPL) will form rectangular imaging grids on either side of the axis of rotation (second and third encoding direction). A cross section through the proposed scanner setup is shown in FIG. 1 while FIG. 2 shows an example of 100 FFP traversal positions through an IPL together with a suitable set of detection coils. The magnet layouts required for generating the FFP pattern in FIG. 2 is shown in an axial view in FIG. 3 and a view of the magnet layout in one quadrant of the wheel is shown in FIG. 4.

Resolution Enhancement Coils (Shift Coils)

For practically realizable sizes of wheels and magnets, the number of stations on the perimeter is limited. As already proposed for other MPI scanners (see Reference [10]), it is possible to add lateral shift coils to the scanner setup as shown in FIG. 1. In contrast to the focus field coils implemented in previous FFP scanners which need to provide large FFP shifts, these coils only need to provide small offset fields so they do not require high powers. By applying small current steps after each wheel rotation it is possible to reach intermediate FFP traversal paths.

Magnet Arrangement for FFL Scanning

If neighboring magnets have identical polarity, and no gaps are left between, then a circular field free line (FFL) is obtained as shown for one quadrant. Lateral and radial offsets of magnet pairs can be used to superimpose an undulating pattern on the FFL. The FFL intersects the IPL at two positions on either side of the rotation axis. During rotation, the undulating pattern will cause a smooth movement of the intersection points over an area determined by the magnet pattern. When a sample is positioned in the FFL path, the signal at any given point of time originates from the Super-Paramagnetic Iron Oxide Nano-Particles currently traversed by the FFL. For unraveling the Super-Paramagnetic Iron Oxide Nano-Particles distribution, the FFL must hit each spatial region multiple times during each cycle. Additionally, an array of detection coils arranged along the rotation direction can be used to resolve the distribution via sensitivity encoding.

Symmetry Requirements on Magnet Placement

To keep the rotating wheels balanced, the magnet pairs on opposite sides of the wheels preferably exhibit identical radial displacements. A straightforward setup uses a two-fold rotational symmetry around the axis of rotation or inversion symmetry about a point located between both wheels on the axis. In the first case, one rotation of the setup constitutes two field cycles, and identical field sequences are created at opposite sides of the axis. In the second case, one rotation constitutes one field cycle. As this provides more encoding positions, this is the preferred arrangement.

Detection and Compensation Coils

The inversion symmetry of the magnet pairs implies that identical field geometries are present on opposite sides of the double wheel arrangement except for inversion of the axial field direction. If identical sets of detection coils are installed on opposite sides of the rotating wheel arrangement, then the passing permanent magnet induce identical voltages in opposite coil pairs. When these are interconnected with appropriate polarity, the signals cancel each other. By careful adjustment of the magnet positions, this cancellation can be optimized more easily than that in typical gradiometer coil setups.

2. Remarks and Notes

Mechanical Movement as a Replacement for Electromagnetic Field Control

The design is a deviation from the development path of previous scanners, where the undesirable mechanical movement of the imaging object was replaced by adding more degrees of freedom to the magnetic shifting of the FFR. The novelty in the design presented here is that instead moving of the imaging object, the magnets defining the selection field are moved, and the arrangement of the magnets on rotating wheels allows to conveniently achieve FFR speeds comparable to those realizable by AC driven coils.

Non-Sinusoidal Field Variation

The scanner design gives up the idea of sinusoidal field variations and FFP paths. Instead, the FFPs travel through the FOV with constant speed along a circular path. Hence, the resulting signals cannot be meaningfully be interpreted in terms of harmonics generation. Receive filters are not required, as the non-harmonic excitation signal is perfectly filtered out by the compensation coil arrangement. In contrast to current FFP scanners, the full Super-Paramagnetic Iron Oxide Nano-Particles signal can be measured, allowing a straight-forward X-space reconstruction.

Gradient Strengths and FOV Sizes

The strongest available permanent magnets have flux densities of about $B_0=1.3$ T on their surface. For magnet poles that are large compared to the distance d between the gradient generating magnets, the maximum gradient strength can be estimated as $G_{max}=2B_0/d$. Neglecting space for the detection coils, the required pole gap is twice the Field of View extent since the FFP that is located at the middle position between the magnets must be shifted over the entire Field of View. For a Field of View extent of 3 cm, one realistically obtains $G_{max}=2\text{-}15$ T/m. In a conventional FFP scanner, shifting the FFP of a 15 T/m gradient by drive field coils over a distance of ±15 mm would require an unreasonable drive field amplitude of 225 mT. This highlights the advantage of the rotating wheel setup. For larger Field of Views and for smaller magnet segments, the achievable gradients are much smaller. This suggests that the new scanner layout may be particular useful for MPI microscopy.

3. Example Numbers

A wheel of 1 m diameter has a circumference of around 3 m. When using magnet slices of 3 cm thickness, one can place 100 such slices around the circumference, with 375 discrete field layouts per image (see example figures). Rotation speeds up to 50/s are realistic, implying an FFP speed of 150 m/s or 540 km/h.

4. Further Ideas Regarding the Invention

Multiple acquisition stations can be installed around the wheels, allowing simultaneous studies on more than one subject.

The magnet element sequence could include mostly homogeneous sections with a certain B field strength. By application of RF pulses synchronized to the rotation the acquisition of MR reference images will be possible.

Instead of two wheels with a gap, the magnets could be mounted on either side of a groove near the border of a single rotating wheel.

Longer sequences, and a straight field of view can be obtained if the magnet pairs are mounted on a "conveyor belt" that is guided along a rigid path. However, such a design is more difficult to implement.

The two wheels could be driven by independent motors, thus realizing more complex field patters resulting from the interference of the installed magnetic fields.

When alternating homogeneous fields are created, a variable frequency MPS spectrometer can be obtained. By varying the field strength along the cycle, a spectrometer can be built that performs multi-frequency/multi-amplitude scanning during a single experiment.

Instead of two moving, magnet holding structures like a transport or conveyor belt or a wheel, only one moving structure may be used in connection with at least one electromagnet synchronized with the motion of the array of permanent magnets. The electromagnet would adapt the magnetic field accordingly to achieve a FFR for every different magnet position.

The variation of permanent magnet position may be established in only one or two dimensions. A motorized sample holder may then shift the sample to bring further sample points into the detection volume.

5. Comparison of the Present Invention to Current MPI Designs

Advantages

Strong selection field gradients possible (high resolution)

Large field of view possible, in particular along wheel perimeter

Change of excitation frequency straightforward

No expensive transmit amplifiers

No expensive transmit filters

No expensive, highly linear resonant circuit

No cooling efforts

Straight-forward implementation of compensation coils

Low or no receive-filtering requirements

6. Distinction to Existing Scanner Concepts

The most similar scanner concept to the presented design is the TWMPI scanner. There is also a similarity to the Ultra-High gradient experiments presented by the TWMPI group.

Differences to TWMPI Scanner

The proposed new scanner design can be regarded as a generalized concept of the TWMPI scanner with the following important new concepts and advantages:

The coil array that produces the moving FFP is replaced by a set of permanent magnets arranged on rotating wheels.

A variation in excitation frequency/scanning speed is easily realizable by changing the speed of rotation, as no resonant circuits are involved.

The gradient orientation is perpendicular to the scanning direction.

By placing magnet pairs at different radial and lateral offsets, a 3D scanner without shift coils is realized.

The scanner can be realized both as an FFP and FFL scanner.

By using inherent symmetry requirements of a rotating wheel design, a detection coil design can be realized that provides a strong suppression of the excitation signal without a direct gradiometer coil.

Differences to Ultra-High Gradient Scanning Experiments

The reported experiments on ultra-high gradient MPI used two magnet rings aligned on a single axis to generate a strong gradient field. A 1D line profile was realized by movement of a sample through the FFP located on the axis between the two rings. The setup will also exhibit a FFL between the rings, which is similar to the present proposal with the following major new concepts:

The magnet rings are split into smaller segments which are placed at different offsets to provide a spatial encoding.

Instead of the FFP on the axis, the FFL (or sequence of FFPs) between the actual rings are used for image generation.

Instead of a sample movement along the axis, the rings are rotated.

Differences to Previous FFL Scanners

The proposed new scanner design can be realized either as an FFP or FFL scanner. In an FFL setup, the following new concepts are present:

No electromagnetic coils are required for the basic encoding and FFL movement.

Instead of a straight line, the FFL is realized as a circle with arbitrarily induced undulations.

A variation in excitation frequency/scanning speed is easily realizable by changing the speed of rotation, as no resonant circuits are involved.

By using inherent symmetry requirements of the rotating wheel design, a detection coil design can be realized that provides a strong suppression of the excitation signal without a direct gradiometer coil.

Differences to Previous FFP Scanners

The proposed new scanner design can be realized either as an FFP or FFL scanner. In an FFP setup, the following new concepts are present:

No electromagnetic coils are required for the basic encoding and FFP movement.

Higher images resolutions are possible without sacrificing FOV size.

In contrast to early scanners with mechanical object movement, the rotating wheel concept allows fast 3D encoding.

CONCLUSION

A new MPI scanner topology based on rotating permanent magnets is proposed which avoids the high power requirements of current MPI scanners, while opening the way for higher spatial resolutions and variable scanning frequencies. An apparatus for Magnetic Particle Imaging at variable operating frequencies is proposed based on a set of moved, in particular rotating, permanent magnets for generating suitable time-varying magnetic fields and a set of detection and compensation coils for ideal suppression of excitation signals.

ABBREVIATIONS

MPI Magnetic Nanoparticle Imaging
FOV Field Of View
FFR Field-Free Region
FFP Field-Free Point
FFL Field-Free Line
IPL Imaging Plane DF Drive Field
SF Selection Field
FF Focus Field
SPIO Super-Paramagnetic Iron Oxide
NP Nanoparticle

REFERENCES

[1] B. Gleich, J. Weizenecker, *Nature* 2005, 435, 1214
[2] J. Weizenecker, B. Gleich, J. Rahmer, H. Dahnke, J. Borgert, *Phys. Med. Biol.* 2009, 54, L1
[3] P. W. Goodwill, K. L. Lu, B. Zheng, S. M. Conolly, *Rev. Sci. Instrum.* 2012, 83, 033706
[4] J. Weizenecker, B. Gleich, J. Borgert, *J. Phys. D: Appl. Phys.* 2008, 41, 105009
[5] T. Knopp, M. Erbe, S. Biederer, T. F. Sattel, T. M. Buzug, *Med. Phys.* 2010, 37, 3538
[6] M. Erbe, T. Knopp, T. F. Sattel, S. Biederer, T. M. Buzug, *Med. Phys.* 2011, 38, 5200
[7] P. W. Goodwill, J. J. Konkle, B. Zheng, E. U. Saritas, S. M. Conolly, *IEEE Transactions on Medical Imaging* 2012, 31, 1076
[8] P. Klauer, M. A. Rückert, P. Vogel, W. H. Kullmann, P. M. Jakob, V. C. Behr, *Proc. Intl. Soc. Mag. Res. Med.* 2011, 19, 3783
[9] P. Vogel, M. A. Rückert, P. M. Jakob, V. C. Behr, *IEEE Trans. Magn.* 2014, announced (presented during International Workshop on Magnetic Particle Imaging (IWMPI) 2014
[10] A. Timmermeyer, H. Wojtczyk, W. Tenner, G. Bringout, M. Grüttner, M. Graeser, T. F. Sattel, A. Halkola, T. M. Buzug, Super-resolution approaches for resolution enhancement in magnetic particle imaging, International Workshop on Magnetic Particle Imaging (IWMPI) 2013, Abstract 43

The invention claimed is:

1. MPI-(=Magnetic Particle Imaging) apparatus comprising a magnet system designed for the generation of a time-varying and position-dependent magnetic field in a detection volume and a detection system detecting signals from MPI contrast agents exposed to said magnetic field within said detection volume, said signals being suitable for reconstructing an image of the spatial—and where required also temporal—distribution of said MPI contrast agents, characterized in that the magnet system comprises an array with a plurality of permanent magnetic elements geometrically arranged in such a way that at least a part of the plurality of permanent magnetic elements are moved with sufficient speed to create the spatial and temporal magnetic field variations for inducing within the contrast agent the MPI signals recorded by the detection system, wherein the magnetic elements are geometrically arranged in the form of one or more rotatable wheels, in particular with the magnetic elements being positioned in a plane parallel to the plane of the wheel.

2. MPI-apparatus according to claim 1, characterized in that the magnetic elements are arranged in neighboring pairs whereby the magnetic elements of each pair have opposite polarity, respectively.

3. MPI-apparatus according to claim 1, characterized in that the magnetic elements are geometrically arranged on one or more transport or conveyor belts in the form of closed loops.

4. MPI-apparatus according to claim 1, characterized in that at least two rotatable wheels are geometrically arranged in a coaxial manner relative to each other.

5. MPI-apparatus according to claim 1, characterized in that the magnetic elements are arranged radially within a closed loop or a wheel.

6. MPI-apparatus according to claim 1, characterized in that at least some of the rotatable wheels are geometrically arranged in a non-coaxial manner relative to each other.

7. MPI-apparatus according to claim 5, characterized in that the closed loops or wheels are movable at variable speed.

8. MPI-apparatus according to claim 7, characterized in that the at least two closed loops or wheels are moveable at different speeds.

9. MPI-apparatus according to claim 5, characterized in that the detection system comprises at least two detection coils arranged at positions of equivalent magnetic field change between neighboring permanent magnetic elements, in particular at opposite positions of the rotatable closed loops or wheels.

10. MPI-apparatus according to claim 9, characterized in that each pair of magnetic elements is complemented by another pair of magnetic elements being positioned on an opposite side of the wheel with respect to the axis of the wheel and that each of complementary pairs is positioned at identical radial displacement with respect to said axis.

11. MPI-apparatus according to claim 1, characterized in that the magnetic elements are arranged in a way such as to provide spatial encoding of the MPI contrast agent within the detection volume.

12. MPI-apparatus according to claim 1, characterized in that the magnetic elements are arranged in a way such as to produce a sinusoidal varying magnetic field at a defined position within the detection volume.

13. MPI-apparatus according to claim 1, characterized in that the magnetic elements are arranged in way to allow for driving the MPI-apparatus in a FFL (=field free line) or in a FFP (=field free point) mode.

14. MPI-apparatus according to claim 1, further comprising auxiliary coils for generating an offset field to shift spatial encoding of the MPI contrast agent within the detection volume.

15. MPI-(=Magnetic Particle Imaging) apparatus comprising a magnet system designed for the generation of a time-varying and position-dependent magnetic field in a detection volume and a detection system detecting signals from MPI contrast agents exposed to said magnetic field within said detection volume, said signals being suitable for reconstructing an image of the spatial—and where required also temporal—distribution of said MPI contrast agents, characterized in that the magnet system comprises an array with a plurality of permanent magnetic elements geometrically arranged in such a way that at least a part of the plurality of permanent magnetic elements are moved with sufficient speed to create the spatial and temporal magnetic field variations for inducing within the contrast agent the MPI signals recorded by the detection system, wherein the magnetic elements are arranged in neighboring pairs whereby the magnetic elements of each pair have opposite polarity, respectively, wherein at least one pair of magnetic elements is arranged in a way to generate homogenous magnetic field section suitable for MRI (=magnetic resonance imaging) by parallel orientation of their respective magnetic field.

* * * * *